(12) United States Patent
Yoshida et al.

(10) Patent No.: US 8,222,283 B2
(45) Date of Patent: Jul. 17, 2012

(54) METHOD FOR TREATING A KERATOCONJUNCTIVAL DISORDER

(75) Inventors: Atsushi Yoshida, Ikoma (JP);
Shinichirou Hirai, Ikoma (JP);
Masatsugu Nakamura, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 60 days.

(21) Appl. No.: 11/920,477

(22) PCT Filed: May 17, 2006

(86) PCT No.: PCT/JP2006/309797
§ 371 (c)(1),
(2), (4) Date: Nov. 15, 2007

(87) PCT Pub. No.: WO2006/123676
PCT Pub. Date: Nov. 23, 2006

(65) Prior Publication Data
US 2009/0105313 A1    Apr. 23, 2009

(30) Foreign Application Priority Data

May 17, 2005  (JP) .................. 2005-143477

(51) Int. Cl.
*A61K 31/42* (2006.01)
(52) U.S. Cl. ...................... 514/359; 514/912
(58) Field of Classification Search ............. 514/359, 514/912
See application file for complete search history.

(56) References Cited

U.S. PATENT DOCUMENTS

| | | | |
|---|---|---|---|
| 4,757,063 | A | 7/1988 | Parnham |
| 4,778,814 | A | 10/1988 | Cash |
| 6,342,510 | B1 | 1/2002 | Isakson et al. |
| 6,525,040 | B1 | 2/2003 | Erdelmeier et al. |
| 2002/0037854 | A1 | 3/2002 | Breton et al. |
| 2002/0107276 | A1 | 8/2002 | Isakson et al. |
| 2003/0166632 | A1* | 9/2003 | Ueno .................. 514/211.07 |
| 2003/0216290 | A1 | 11/2003 | Lecomte et al. |
| 2010/0120873 | A1 | 5/2010 | Hirai et al. |
| 2011/0009376 | A1 | 1/2011 | Hirai et al. |

FOREIGN PATENT DOCUMENTS

| | | |
|---|---|---|
| EP | 0249735 A2 | 12/1987 |
| EP | 0249735 A3 | 12/1987 |
| JP | 2001-261555 A | 9/2001 |
| JP | 2006-104199 A | 4/2006 |
| JP | 2008-13448 A | 1/2008 |
| WO | WO 2004/069157 A | 8/2004 |
| WO | WO 2004/071419 A2 | 8/2004 |
| WO | WO 2006/123676 A1 | 11/2006 |
| WO | WO 2008/146721 A1 | 12/2008 |

OTHER PUBLICATIONS

Zhang et al., Free Radical Biology & Medicine, vol. 32, No. 5, pp. 454-464, 2002.*
J. Cai et al., "Oxidative Damage and Protection of the RPE," *Progress in Retinal and Eye Research*, 2000, vol. 19, No. 2, pp. 205-221.
U.S. Appl. No. 12/451,368; Confirmation No. 1450.
International Search Report for PCT/JP2008/059503 mailed Jul. 15, 2008.
G. Tomita et al., Ophthalmology, 1998, pp. 251-273, vol. 40, No. 3.
H. Abe et al., "Optic nerve", Ophthalmology, 2002, pp. 1413-1416, vol. 44, No. 11.
S. Lipton, "Possible Role for Memantine in Protecting Retinal Ganglion Cells from Glaucomatous Damage", Survey of Ophthalmology, Apr. 2003, pp. S38-S46, vol. 48.
D.G. Buerk, "Ebselen improves recovery of electroretinogram after ischemia/reperfusion in rabbit eye", sourced from Faseb Journal, 2004, pp. Abst. 429.13, vol. 18, No. 4-5.
F.B. Centuriao et al., "Effect of ebselen and organochalcogenides on excitotoxicity induced by glutamate in isolated chick retina", Brain Research, 2005, pp. 146-152, 1039.
C.A. Girkin, "Neuroprotection: Does it Work for all Neurological Diseases?", Clinical & Surgical Journal of Ophthalmology, 2006, pp. 362-367, 24 (9).
B. Gabryel et al., "Ebselen attenuates oxidative stress in ischemic astrocytes depleted of glutathione. Comparison with glutathione precursors", Pharmacological Reports, 2006, pp. 381-392, 58.
Q. Liu et al., "Oxidative Stress Is an Early Event in Hydrostatic Pressure-Induced Retinal Ganglion Cell Damage", Investigative Ophthalmology & Visual Science, Oct. 2007, pp. 4580-4589, vol. 48, No. 10.
A. Izzotti et al., "The role of oxidative stress in glaucoma", Mutation Research, 2006, pp. 105-114, 612.
Mayumi Okada, "Ryokunaisho o Meguru Wadai III. Ryokunaisho no Chiryo Shinkei Hogo to Yakubutsu Ryoho", Kowa Iho, 2000, pp. 13-18, 43 (2).
N. Calandrella et al., "Degenerative and apoptotic events at retinal and optic nerve level after experimental induction of ocular hypertension", Molecular and Cellular Biochemistry, 2007, pp. 155-163, 301 (1-2).

(Continued)

*Primary Examiner* — Zohreh Fay
(74) *Attorney, Agent, or Firm* — Holtz, Holtz, Goodman & Chick, P.C.

(57) ABSTRACT

An object of the present invention is to provide a new medicinal use of 2-phenyl-1,2-benzisoselenazol-3(2H)-one or a salt thereof. 2-Phenyl-1,2-benzisoselenazol-3(2H)-one or a salt thereof exhibits an excellent prevention and improvement effect in corneal disorder models, and is therefore useful as a preventive or therapeutic agent for a keratoconjunctival disorder such as dry eye, superficial punctate keratopathy, corneal epithelial defects, corneal erosion, corneal ulcer, conjunctival epithelial defects, keratoconjunctivitis sicca, superior limbic keratoconjunctivitis, filamentary keratoconjunctivitis, keratitis or conjunctivitis.

1 Claim, No Drawings

OTHER PUBLICATIONS

G.A. Herin et al., "The neuroprotective agent ebselen modifies NMDA receptor function via the redox modulatory site", Journal of Neurochemistry, 2001, pp. 1307-1314, 78 (6).

J.Z. Nowak, "Age-related macular degeneration (AMD): pathogenesis and therapy," *Pharmacological Reports*, 2006, 58, pp. 353 to 363.

S. Boger et al., "Antioxidants may reduce the risk for age-related maculopathy in populations with high ocular exposure to solar radiation," *Journal of the American Dietetic Association*, 1999, 99(9), Supplement 1, A-45.

F. Bosch-Morell et al., "Efficacy of the antioxidant ebselen in experimental uveitis" *Free Radical Biology & Medicine*, 1999, vol. 27, Nos. 3/4, pp. 388-391.

J.J. Khatri et al., "Vascular Oxidant Stress Enhances Progression and Angiogenesis of Experimental Atheroma," *Circulation*, 2004, 109, pp. 520-525.

D.G. Herrera et al., "Selective impairment of hippocampal neurogenesis by chronic alcoholism: Protective effects of an antioxidant," *PNAS*, 2003, vol. 100, No. 13, pp. 7919-7924.

T. Tojo et al., "Role of gp91$^{phox}$ (Nox2)-Containing NAD(P)H Oxidase in Angiogenesis in Response to Hindlimb Ischemia," *Circulation*, 2005; vol. 111, pp. 2347-2355.

O. Gealekman et al., "Endothelial dysfunction as a modifier angiogenic response in Zucker diabetic fat rat: Amelioration with Ebselen," *Kidney International*, 2004, vol. 66, pp. 2337-2347.

Supplementary European Search Report dated Dec. 3, 2009 for European patent application EP 06 746 500.5.

Stefano Barabino et al., "Systemic Linoleic and γ-Linolenic Acid Therapy in Dry Eye Syndrome With an Inflammatory Component," *Cornea*, 22(2), 97-101, (2003).

Dianne Petrone et al., "A Double-Blind, Randomized, Placebo-Controlled Study of Cevimeline In Sjögren's Syndrome Patients With Xerostomia and Keratoconjunctivitis Sicca," *Arthritis & Rheumatism*, vol. 46, No. 3, Mar. 2002, pp. 748-754.

Frederick B. Vivino et al., "Pilocarpine Tablets for the Treatment of Dry Mouth and Dry Eye Symptoms in Patients with Sjögren Syndrome," *Archives of Internal Medicine*, 159(2), 174-181, (1999).

John S. Hurst et al., "Effects of ebselen on arachidonate metabolism by ocular and nonocular tissues", *Biochemical Pharmacology*, vol. 38, No. 19, pp. 3357-3363 ((1989).

Rumi Imaoka et al, "Studies on ocular pharmacology (Rept. 32): Beneficial effect of EPC-K1, a novel antioxidant, . . . ", *Japanese Journal of Pharmacology*, vol. 82, No. Suppl. 1, p. 273P (2000).

Teruo Nishida et al, "Clinical classification of the corneal epithelial disorders", *Clinical Ophthalmology*, 46, pp. 738-743 (1992) (Abstract on last page).

Chikako Katakami, "A New Treatment for Corneal Epithelial Defects Using Fibronectin, EGF and Hyaluronic Acid", *Ophthalmic Surgery*, 5, pp. 719-727 (1992).

Daniel G. Herrera et al, "Selective impairment of hippocampal neurogenesis by chronic alcoholism: Protective effects of an antioxidant", *Proceedings Natl. Acad. Sci. USA*, 100 (13), pp. 7919-7924 (2003).

* cited by examiner

METHOD FOR TREATING A KERATOCONJUNCTIVAL DISORDER

This application is the United States national phase application of International Application PCT/JP2006/309797 filed May 17, 2006.

TECHNICAL FIELD

The present invention relates to a preventive or therapeutic agent for a keratoconjunctival disorder such as dry eye, superficial punctate keratopathy, corneal epithelial defects, corneal erosion, corneal ulcer, conjunctival epithelial defects, keratoconjunctivitis sicca, superior limbic keratoconjunctivitis, filamentary keratoconjunctivitis, keratitis or conjunctivitis, comprising 2-phenyl-1,2-benzisoselenazol-3(2H)-one or a salt thereof as an active ingredient.

BACKGROUND ART

Cornea is a transparent avascular tissue having a diameter of about 1 cm and a thickness of about 1 mm, while conjunctiva is a mucosal membrane covering the eyeball surface posterior to the corneal margin, and the back face of the eyelid. The cornea and the conjunctiva are known to significantly affect the visual function. Keratoconjunctival disorders caused due to a variety of diseases such as corneal ulcer, keratitis, conjunctivitis and dry eye may adversely affect normal construction of epithelium, and furthermore, may impair structures and functions of the corneal stroma and endothelium, when the repair of these disorders is retarded, alternatively when these disorders are prolonged without making repair on some grounds. That is because the cornea and the conjunctiva are connected tissues. In these years, with the development of cell biology, factors participating in cell proliferation, migration, adhesion, extension, differentiation and the like had been elucidated, and it was reported that these factors play important roles in repair of corneal disorders (Japanese Review of Clinical Ophthalmology, 46, 738-743 (1992), Ophthalmic Surgery, 5, 719-727 (1992)).

On the other hand, Proc. Natl. Acad. Sci. USA, 100 (13), 7919-7924 (2003) describes that 2-phenyl-1,2-benzisoselenazol-3(2H)-one (generic name: ebselen, hereinafter referred to as "ebselen") has an antioxidant activity, and JP-A-2001-261555 describes that ebselen is effective as a therapeutic agent for cerebral arteriosclerosis and chronic cerebral circulatory failure.

However, there is no report of study on a pharmacological effect of such a compound on an eye disease such as a keratoconjunctival disorder.

DISCLOSURE OF THE INVENTION

Problems to be Solved

It is an interesting subject to search a new medicinal use of ebselen.

Means of Solving Problems

The present inventors have made intensive studies in order to search a new medicinal use of the above-mentioned compound, and as a result, they found that the above-mentioned compound or a salt thereof exhibits an excellent effect of preventing and improving a corneal damage in a test for therapeutic effect using corneal disorder models and the like, and thus the present invention has been accomplished. Incidentally, the same test was also carried out using known compounds having an antioxidant effect similar to ebselen, however, ebselen exhibited a far superior effect to these known compounds, which supports the excellent usefulness of ebselen.

That is, the present invention is directed to a preventive or therapeutic agent for a keratoconjunctival disorder such as dry eye, superficial punctate keratopathy, corneal epithelial defects, corneal erosion, corneal ulcer, conjunctival epithelial defects, keratoconjunctivitis sicca, superior limbic keratoconjunctivitis, filamentary keratoconjunctivitis, keratitis or conjunctivitis, comprising ebselen or a salt thereof as an active ingredient.

Ebselen of the present invention is a condensed heterocyclic compound represented by the following chemical structural formula [I].

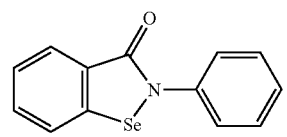

[I]

The salt of the above-mentioned compound is not particularly limited as long as it is a pharmaceutically acceptable salt, and examples thereof include salts with an inorganic acid such as hydrochloric acid, nitric acid or sulfuric acid, salts with an organic acid such as acetic acid, fumaric acid, maleic acid, succinic acid or tartaric acid, and the like. Incidentally, the above-mentioned compound may be in a form of a solvate.

In the present invention, the keratoconjunctival disorder means the state of damaged cornea and/or conjunctiva due to various causes such as tear abnormality, metabolic abnormality and external damage, and examples thereof include dry eye, superficial punctate keratopathy, corneal epithelial defects, corneal erosion, corneal ulcer, conjunctival epithelial defects, keratoconjunctivitis sicca, superior limbic keratoconjunctivitis, filamentary keratoconjunctivitis, keratitis, conjunctivitis and the like. Further, dry eye as stated herein mean decreased tear production, xerophthalmia, tear deficiency, Sjogren's syndrome, keratoconjunctivitis sicca, Stevens-Johnson syndrome, lacrimal gland dysfunction, meibomian gland dysfunction, blepharitis, a keratoconjunctival disorder due to VDT (visual display terminal) operation, surgery, a drug, an external damage, use of contact lenses, etc., or symptoms accompanied by the keratoconjunctival disorder.

The preventive or therapeutic agent for a keratoconjunctival disorder of the present invention can be administered either orally or parenterally (instillation, transdermal administration or the like). Examples of the dosage form include eye drops, ophthalmic ointments, skin ointments, injections, tablets, capsules, granules, fine granules, powders and the like. These can be prepared using any of widely used techniques. For example, the eye drop can be prepared using a tonicity agent such as sodium chloride or concentrated glycerin, a buffer such as sodium phosphate or sodium acetate, a surfactant such as polyoxyethylene sorbitan monooleate, polyoxyl 40 stearate or polyoxyethylene hydrogenated castor oil, a stabilizer such as sodium citrate or sodium edetate, a preservative such as benzalkonium chloride or paraben as needed. The pH of the eye drop is permitted as long as it falls within the range that is acceptable as an ophthalmic preparation, but is preferably in the range of from 4 to 8.

The ophthalmic ointment can be prepared with a widely used vehicle such as white soft paraffin or liquid paraffin. Oral preparations such as tablets, capsules, granules, fine granules and powders can be prepared using an extender such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicone resin, a film forming agent such as gelatin film, and the like, as needed.

The present invention also relates to a method for preventing or treating a keratoconjunctival disorder comprising administering a pharmacologically effective amount of 2-phenyl-1,2-benzisoselenazol-3(2H)-one or a salt thereof to a patient.

The dose of the above-mentioned compound can be properly selected depending on the symptoms, age, dosage form and the like. In the case of an eye drop, it may be instilled once to several times a day at a concentration of from 0.000001 to 1% (w/v), preferably from 0.0001 to 0.1% (w/v). In the case of an oral preparation, it may be administered once or divided into several times at a dose of generally from 0.1 to 5000 mg per day, preferably from 1 to 1000 mg per day.

Advantage of the Invention

As will be described below, when the following pharmacological test was carried out, ebselen exhibits an excellent prevention and improvement effect in corneal disorder models. Therefore ebselen is useful as a preventive or therapeutic agent for a keratoconjunctival disorder such as dry eye, superficial punctate keratopathy, corneal epithelial defects, corneal erosion, corneal ulcer, conjunctival epithelial defects, keratoconjunctivitis sicca, superior limbic keratoconjunctivitis, filamentary keratoconjunctivitis, keratitis or conjunctivitis.

BEST MODE FOR CARRYING OUT THE INVENTION

Hereinafter, results of a pharmacological test and preparation examples will be described, however, these examples are for understanding the present invention well, and are not meant to limit the scope of the present invention.
[Pharmacological Test]
1. Test for Therapeutic Effect on Corneal Damage Using Rats in which the Exorbital Lacrimal Gland was Removed Using male SD rats, corneal disorder models were produced in accordance with the method of Fujihara et al. (Invest. Opthalmol. Vis. Sci. 42 (1): 96-100 (2001)). After the production of the corneal disorder models, the improvement ratio of corneal damage was evaluated by a method (Journal of the eye 21 (1): 87-90 (2004)) modified from the method of Miyata et al. (Japanese Review of Clinical Ophthalmology 48 (2) 183-188 (1994)).
(Test Method)

Male SD rats were systemically anesthetized by an administration of Nembutal. Subsequently, the exorbital lacrimal gland of each rat was removed and a corneal damage was induced over a period of 2 months.

Subsequently, ebselen was administered as follows. As comparative compounds, 3-methyl-1-phenyl-2-pyrazolin-5-one represented by the following formula [II] (hereinafter referred to as "edaravone") and (3R)-1,2-dithiolane-3-pentanoic acid represented by the following formula [III] (hereinafter referred to as "α-lipoic acid") were administered as follows. Edaravone and α-lipoic acid are known to have an antioxidant effect (J. Radiat. Res., 45, 319-323 (2004), J. Nutr., 133, 3327-3330 (2003)). Ebselen also has the same effect as described above, therefore, ebselen, edaravone and α-lipoic acid are have a common feature in terms of having such an effect.

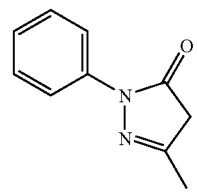

[II]

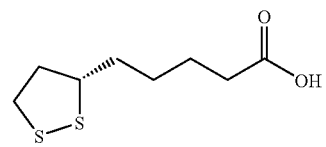

[III]

Ebselen Administration Group:
A physiological saline solution containing ebselen (25 µM) was instilled into both eyes 6 times a day for 14 days (one group consisting of 8 animals).
Edaravone Administration Group:
A physiological saline solution containing edaravone (200 µM) was instilled into both eyes 6 times a day for 14 days (one group consisting of 8 animals).
α-Lipoic Acid Administration Group:
A physiological saline solution containing α-lipoic acid (200 µM) was instilled into both eyes 6 times a day for 14 days (one group consisting of 8 animals).

In a control group, physiological saline was instilled into both eyes 6 times a day for 14 days (one group consisting of 8 animals)

Fourteen days after the start of instillation, the damaged parts of the cornea were stained with fluorescein. For each of the upper, middle and lower parts of the cornea, the degree of fluorescein staining was evaluated by scoring according to the criteria shown below and the improvement ratio of corneal damage was calculated from the mean value of the total scores for each of the above-mentioned parts.
(Evaluation Criteria)
0: No punctate staining
1: Scattered staining (punctate staining being separated)
2: Moderate staining (a part of punctate staining being adjacent)
3: Heavy staining (punctate staining being barely separated)
Incidentally, intermediate values (at intervals of 0.5) were set between the respective scores.
(Results)

By taking the mean value of the scores for the control group (physiological saline) as a standard (improvement ratio: 0%) and according to the calculation equation shown below, the improvement ratios for the ebselen (25 µM) administration group and the edaravone (200 µM) administration group and α-lipoic acid (200 µM) administration group were calculated, respectively, which are shown in Table 1. Incidentally, the mean value of the scores is a mean of those of 8 cases in each group.

Improvement ratio (%)={(control)−(administered compound)}/damage degree×100

Damage degree=(control)−(normal eye)

TABLE 1

| Test group | Improvement ratio (%) |
|---|---|
| Ebselen (25 μM) administration group | 76.5 |
| Edaravone (200 μM) administration group | 36.9 |
| α-Lipoic acid (200 μM) administration group | 30.8 |

(Discussion)

As apparent from the results of the above-mentioned pharmacological test using rats, ebselen exhibits a more remarkable improvement ratio compared with edaravone and α-lipoic acid. In particular, it is a surprising result that ebselen exhibits an improvement ratio which is more than twice as high as those of edaravone and α-lipoic acid although ebselen was administered in an amount of one-eighth of the concentration of edaravone and α-lipoic acid. Thus, it was shown that ebselen has a remarkable effect of improving a keratoconjunctival disorder.

2. Pharmacological Test Using SAMP10

Using senescence-accelerated mouse model P10 (hereinafter referred to as SAMP10), an effect of ebselen on a corneal damage was evaluated in accordance with the method of Hirai, Shibagaki et al. (JP-A-2006-104913). Incidentally, as a control animal, SAMR1 with normal senescence was used.

(Test Method)

SAMP10 develops a corneal disorder with aging. Accordingly, a corneal damage of female SAMP10 at 16 weeks of age (before a change caused by aging is observed) was evaluated, and then, administration of an ebselen solution or its vehicle was started. At 8 weeks after the start of administration (at 24 weeks of age), the same evaluation was carried out again. In the same manner, a corneal damage of female SAMR1 at 16 weeks of age was evaluated, and thereafter, administration of the above-mentioned vehicle was started. Then, at 8 weeks after the start of administration (at 24 weeks of age), the same evaluation was carried out again.

(Administration Method)

Ebselen suspensions obtained by suspending it in a 1% (w/v) methyl cellulose aqueous solution (prepared by dissolving methyl cellulose in ultrapure water) at a concentration of 0.45 mg/mL and 4.5 mg/mL respectively were orally administered to female SAMP10 once a day at a dose of 6.67 μL per g of body weight of mouse. The both administration groups were determined to be a 3 mg/kg group and a 30 mg/kg group, respectively. The administration was carried out 5 days a week (Mon, Tue, Wed, Thu, Fri) over a period of 8 weeks. As a control, a 1% (w/v) methyl cellulose aqueous solution was orally administered to SAMP10 in the same manner at a dose of 6.67 μL per g of body weight of mouse. Further, to the control animal, female SAMR1, a 1% (w/v) methyl cellulose aqueous solution was orally administered in the same manner. Incidentally, the number of animals in each group of SAMP10 is 22 eyes (11 mice), and the number of SAMR1 is 16 eyes (8 mice).

(Evaluation Method)

The damaged parts of the cornea of SAMP10 and SAMR1 were stained with fluorescein immediately before and at 8 weeks after the start of administration. For each of the upper, middle and lower parts of the cornea, the degree of fluorescein staining was evaluated by scoring according to the evaluation criteria described in "1. Test for therapeutic effect on corneal damage using rat models in which the exorbital lacrimal gland was removed", and the scoring of the degree of corneal damage (a maximum score of 9 points) was carried out by obtaining the total scores for each of the above-mentioned parts.

(Results)

The scores of fluorescein staining of SAMP10 and SAMR1 at 16 and 24 weeks of age are shown in Table 2. Incidentally, the scores in the table are expressed as mean±standard error in each group.

TABLE 2

| Strain | Administered agent | Score of fluorescein staining | |
|---|---|---|---|
| | | 16 weeks of age | 24 weeks of age |
| SAMR1 | Vehicle | 2.44 ± 0.34 | 1.69 ± 0.31 |
| SAMP10 | Vehicle | 2.25 ± 0.22 | 4.23 ± 0.43** |
| | Ebselen 3 mg/kg | 2.61 ± 0.38 | 2.95 ± 0.45* |
| | Ebselen 30 mg/kg | 2.45 ± 0.30 | 2.68 ± 0.33* |

**$p < 0.01$: Comparison with SAMR1 (Student's t-test)
*$p < 0.05$: Comparison with the vehicle administration group of SAMP10 (Dunnett's test)

(Discussion)

As apparent from Table 2, at 16 weeks of age, there was no significant difference between the vehicle administration group of SAMR1 and the vehicle administration group of SAMP10 (Student's t-test), and a significant difference between the respective drug administration groups of SAMP10 was not observed (Tukey test) either. At 24 weeks of age, it was observed that the staining score is significantly increased in the vehicle administration group of SAMP10 compared with the vehicle administration group of SAMR1. That is, it was confirmed that SAMP10 develops a corneal disorder with aging. Under these conditions, it was observed that the staining score is significantly decreased in both ebselen administration groups of 3 mg/kg and 30 mg/kg compared with the vehicle administration group of SAMP10. That is, it was confirmed that ebselen has an effect of preventing and improving a corneal disorder.

PREPARATION EXAMPLES

Hereinafter, representative preparation examples using ebselen will be shown.

Preparation Example 1

Eye Drop

| In 100 ml, | |
|---|---|
| Ebselen | 10 mg |
| Sodium Chloride | 900 mg |
| Sterile purified water | q.s. |

By altering the amount of ebselen to be added, an eye drop at a concentration of 0.001% (w/v), 0.03% (w/v), 0.1% (w/v), 0.3% (w/v) or 1.0% (w/v) can be prepared.

Preparation Example 2

Eye Drop

| In 100 ml, | |
|---|---|
| Ebselen | 100 mg |
| Sodium Chloride | 800 mg |
| Disodium hydrogen phosphate | 100 mg |
| Sodium dihydrogen phosphate | q.s. |
| Sterile purified water | q.s. |

By altering the amount of ebselen to be added, an eye drop at a concentration of 0.05% (w/v), 0.3% (w/v), 0.5% (w/v) or 1% (w/v) can be prepared.

Preparation Example 3

Ophthalmic Ointment

| In 100 g, | |
|---|---|
| Ebselen | 0.3 g |
| Liquid paraffin | 10.0 g |
| White soft paraffin | q.s. |

By altering the amount of ebselen to be added, an ophthalmic ointment at a concentration of 1% (w/w) or 3% (w/w) can be prepared.

Preparation Example 4

Tablet

| In 100 mg, | |
|---|---|
| Ebselen | 1 mg |
| Lactose | 66.4 mg |
| Cornstarch | 20 mg |
| Carboxymethyl cellulose calcium | 6 mg |
| Hydroxypropyl cellulose | 6 mg |
| Magnesium stearate | 0.6 mg |

Ebselen and lactose are mixed in a mixer, carboxymethyl cellulose calcium and hydroxypropyl cellulose are added thereto, and the resulting mixture is granulated. The obtained granules are dried and the granule size is selected. Then, magnesium stearate is added and mixed with the granules with selected size and the resulting mixture is tabletted with a tableting machine. Further, by altering the amount of ebselen to be added, a tablet with an ebselen content of 0.1 mg, 10 mg or 50 mg in 100 mg can be prepared.

The invention claimed is:

1. A method for treating a keratoconjunctival disorder, wherein the keratoconjunctival disorder comprises dry eye, and wherein the method comprises orally administering from 3 mg/kg to 30 mg/kg per day of 2-phenyl-1,2-benzisoselenazol-3(2H)-one or a salt thereof to a patient in need thereof.

\* \* \* \* \*